(12) United States Patent
Silverstein

(10) Patent No.: US 7,720,697 B1
(45) Date of Patent: May 18, 2010

(54) SYSTEMS AND METHODS FOR PHARMACY CLAIMS-BASED CONDITION IDENTIFICATION PROXIES

(75) Inventor: Steven Richard Silverstein, Englewood, CO (US)

(73) Assignee: McKesson Financial Holdings Limited (BM)

( * ) Notice: Subject to any disclaimer, the term of this patent is extended or adjusted under 35 U.S.C. 154(b) by 0 days.

(21) Appl. No.: 12/200,441

(22) Filed: Aug. 28, 2008

(51) Int. Cl.
*A61B 5/00* (2006.01)
*G06F 19/00* (2006.01)

(52) U.S. Cl. .......................................... 705/3

(58) Field of Classification Search ................. 705/2, 705/3
See application file for complete search history.

(56) References Cited

U.S. PATENT DOCUMENTS

| | | | |
|---|---|---|---|
| 5,628,530 | A | 5/1997 | Thornton |
| 6,012,035 | A | 1/2000 | Freeman et al. |
| 6,757,898 | B1 | 6/2004 | Ilsen et al. |
| 6,769,228 | B1 | 8/2004 | Mahar |
| 7,155,397 | B2 | 12/2006 | Alexander et al. |
| 2002/0002495 | A1* | 1/2002 | Ullman ................. 705/21 |
| 2002/0087583 | A1 | 7/2002 | Morgan et al. |
| 2002/0111832 | A1* | 8/2002 | Judge ..................... 705/3 |
| 2002/0198831 | A1 | 12/2002 | Patricelli et al. |
| 2003/0009367 | A1 | 1/2003 | Morrison |
| 2003/0050799 | A1 | 3/2003 | Jay et al. |
| 2003/0149625 | A1 | 8/2003 | Leonardi et al. |
| 2003/0154163 | A1 | 8/2003 | Phillips et al. |
| 2003/0229540 | A1 | 12/2003 | Algiene |
| 2004/0039599 | A1 | 2/2004 | Fralic |
| 2004/0073457 | A1 | 4/2004 | Kalies |
| 2004/0078234 | A1 | 4/2004 | Tallal, Jr. |

(Continued)

FOREIGN PATENT DOCUMENTS

CA 2482370 3/2006

(Continued)

OTHER PUBLICATIONS

Sampson, R.J., Taking Control of Health Care Costs, Best's Review—Life Health Insurance Edition, Nov. 1983, pp. 64-66, vol. 84, Issue 7, USA.

(Continued)

*Primary Examiner*—Gerald J. O'Connor
*Assistant Examiner*—Trang Nguyen
(74) *Attorney, Agent, or Firm*—Sutherland Asbill & Brennan LLP

(57) ABSTRACT

Systems and methods may be provided for pharmacy claims-based condition identification proxies. The systems and methods may include receiving, by a condition identification system, at least one pharmacy claim associated with a patient, where each pharmacy claim is associated with a medication previously filled by the patient, and identifying, by the condition identification system, the patient as a candidate for at least one chronic medical condition by analyzing the at least one pharmacy claim associated with the patient. The systems and methods may also include determining, by the condition identification system, a pharmacy home for the patient, and transmitting, by the condition identification system to a pharmacy computer associated with the pharmacy home, an identification of the patient that is the candidate for at least one chronic medical condition, where the patient is offered at least one service by the pharmacy home based upon the transmitted identification of the patient.

18 Claims, 5 Drawing Sheets

U.S. PATENT DOCUMENTS

| | | | |
|---|---|---|---|
| 2004/0111291 A1* | 6/2004 | Dust et al. .................... | 705/2 |
| 2004/0117323 A1 | 6/2004 | Mindala | |
| 2004/0148198 A1 | 7/2004 | Kalies | |
| 2004/0249745 A1 | 12/2004 | Baaren | |
| 2005/0015280 A1 | 1/2005 | Gabel et al. | |
| 2005/0060201 A1 | 3/2005 | Connely et al. | |
| 2005/0102169 A1 | 5/2005 | Wilson | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0240473 A1 | 10/2005 | Ayers et al. | |
| 2005/0288972 A1 | 12/2005 | Marvin et al. | |
| 2006/0020514 A1 | 1/2006 | Yered | |
| 2006/0026041 A1 | 2/2006 | Ullman et al. | |
| 2006/0149784 A1 | 7/2006 | Tholl et al. | |
| 2006/0184391 A1* | 8/2006 | Barre et al. .................... | 705/2 |
| 2006/0259363 A1 | 11/2006 | Jhetam | |
| 2006/0271405 A1* | 11/2006 | Cipolle et al. ................. | 705/3 |
| 2007/0005402 A1 | 1/2007 | Kennedy et al. | |
| 2007/0050209 A1 | 3/2007 | Yered | |
| 2007/0136100 A1 | 6/2007 | Daugherty et al. | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |

FOREIGN PATENT DOCUMENTS

| | | |
|---|---|---|
| WO | 9503569 | 2/1995 |
| WO | 0039737 | 7/2000 |
| WO | 2007025295 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

* cited by examiner

US 7,720,697 B1

SYSTEMS AND METHODS FOR PHARMACY CLAIMS-BASED CONDITION IDENTIFICATION PROXIES

FIELD OF THE INVENTION

Aspects of the invention relate generally to identifying patients with chronic medical conditions through pharmacy claims.

BACKGROUND OF THE INVENTION

Medical claims are typically utilized for identification of patients with chronic medical conditions. However, where medical claims are not available, another solution is required to identify patients with chronic medical conditions. Accordingly, there is a need in the industry for identifying patients with chronic medical conditions through pharmacy claims.

SUMMARY OF THE INVENTION

According to an example embodiment of the invention, there may be a computer-implemented method. The computer-implemented method may include receiving, by a condition identification system, at least one pharmacy claim associated with a patient, where each pharmacy claim is associated with a medication previously filled by the patient, and identifying, by the condition identification system, the patient as a candidate for at least one chronic medical condition by analyzing the at least one pharmacy claim associated with the patient. The computer-implemented method may also include determining, by the condition identification system, a pharmacy home for the patient, and transmitting, by the condition identification system to a pharmacy computer associated with the pharmacy home, an identification of the patient that is the candidate for at least one chronic medical condition, where the patient is offered at least one service by the pharmacy home based upon the transmitted identification of the patient.

According to another example embodiment of the invention, there may be a system. The system may include a memory for storing computer-executable instructions, and a processor configured to access the memory. The memory may be operable to execute the computer-executable instructions to receive, from a payor computer, at least one pharmacy claim associated with a patient, where each pharmacy claim is associated with a medication previously filled by the patient; identify, based upon an analysis of the at least one pharmacy claim, the patient as a candidate for at least one chronic medical condition; determine a pharmacy home for the patient; and transmit, to a pharmacy computer associated with the pharmacy home, an identification of the patient that is the candidate for at least one chronic medical condition, where the patient is offered at least one service by the pharmacy home based upon the transmitted identification of the patient.

BRIEF DESCRIPTION OF THE DRAWINGS

Reference will now be made to the accompanying drawings, which are not necessarily drawn to scale, and wherein.

DETAILED DESCRIPTION

Figure 1:
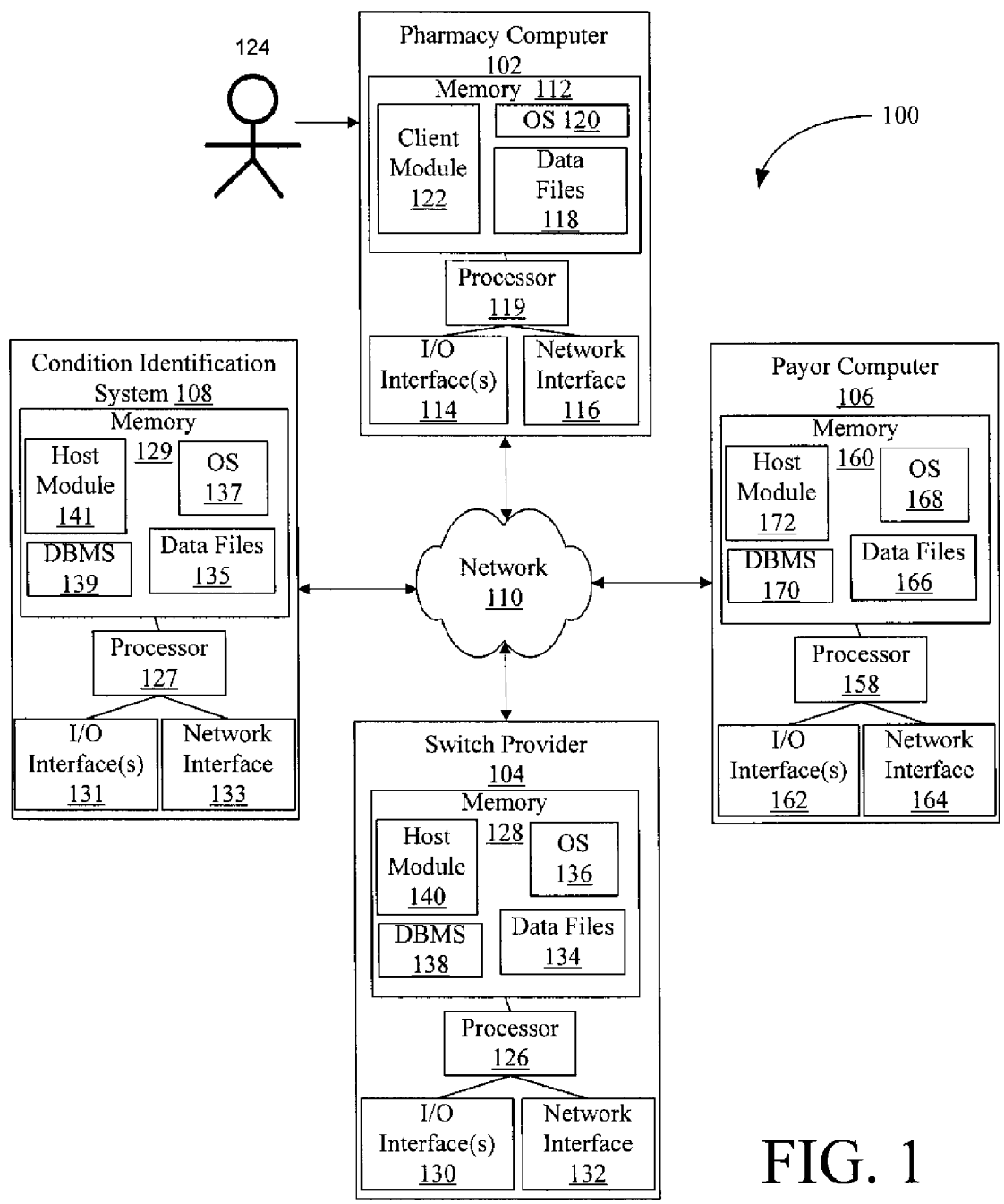
FIG. 1 shows a block diagram of a system for processing pharmacy claims and identifying patients that are candidates for having chronic medical conditions through an analysis of pharmacy claims, according to an example embodiment of the invention.

Example embodiments of the invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those of ordinary skill in the art. Like numbers refer to like elements throughout.

The invention is described below with reference to block diagrams and flowchart illustrations of systems, methods, apparatuses and computer program products according to embodiments of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational elements or steps to be performed on the computer or other programmable apparatus to produce a computer implemented process such that the instructions that execute on the computer or other programmable apparatus provide elements or steps for implementing the functions specified in the flowchart block or blocks.

Accordingly, blocks of the block diagrams and flowchart illustrations support combinations of means for performing the specified functions, combinations of elements or steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

Embodiments of the invention are directed towards the identification of eligible patients that are candidates for having chronic medical conditions through an analysis of pharmacy claims of the respective patients. The identified patients may be offered consultations, services, or information associated with one or more of their chronic medical conditions. As an example, the identified patients may be offered consultations with a pharmacist or other healthcare provider to review their medications, and/or treatments for their chronic medical conditions according to a Medication Therapy Management (MTM) program. The identified patients may likewise be provided with educational or promotional information, including information about enrollment in other MTM programs, coupons, discounts, free samples of drugs, or over-the-counter medications, associated with the chronic medical conditions.

An example system in accordance with an embodiment of the invention is shown in FIG. 1. FIG. 1 shows a block diagram of a system 100 for processing pharmacy claims and identifying patients that are candidates for having chronic medical conditions through an analysis of pharmacy claims, according to an example embodiment of the invention. In particular, the system 100 of FIG. 1 may include at least one pharmacy computer 102, a switch provider 104, at least one payor computer 106, and a condition identification system 108, which are each configured for accessing and reading associated computer-readable media having stored thereon data and/or computer-executable instructions for implementing the various methods described herein. Generally, network devices and systems, including the pharmacy computer 102, switch provider 104, payor computer 106, and condition identification system 108 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 1, a pharmacy computer 102, a switch provider 104, a payor computer 106, and a condition identification system 108 may be in communication with each other via a network 110, which as described below can include one or more private and public networks, including the Internet. Each of these components—the pharmacy computer 102, the switch provider 104, the payor computer 106, the condition identification system 108, and the network 110—will now be discussed in turn.

The pharmacy computer 102 may be any processor-driven device, such as a personal computer, laptop computer, handheld computer, and the like. In addition to having a processor 119, the pharmacy computer 102 may further include a memory 112, input/output ("I/O") interface(s) 114 and a network interface 116. The memory 112 may store data files 118 and various program modules, such as an operating system ("OS") 120 and a client module 122. The client module 122 may be an Internet browser or other software, including a dedicated program, for interacting with the switch provider 104 or another entity, including the condition identification system 108 described herein. For example, a user 124 such as a pharmacist or other pharmacy employee, may utilize the client module 122 in preparing and providing a prescription claim request for delivery to the payor computer 106 via the switch provider 104. The pharmacy computer 102 may also utilize the client module 122 to retrieve or otherwise receive data from the condition identification system 108, including receiving information regarding patients that are candidates for having chronic medical conditions, and that may be eligible for additional services, including Medication Therapy Management (MTM) Programs.

Still referring to the pharmacy computer 102, the I/O interface(s) 114 may facilitate communication between the processor 119 and various I/O devices, such as a keyboard, mouse, printer, microphone, speaker, monitor, bar code readers/scanners, RFID readers, and the like. The network interface 116 may take any of a number of forms, such as a network interface card, a modem, a wireless network card, and the like. These and other components of the pharmacy computer 102 will be apparent to those of ordinary skill in the art and are therefore not discussed in more detail herein.

The switch provider 104 may be operative to route pharmacy claim transactions between the pharmacy computer 102 and one or more payor computers 106, according to an example embodiment of the invention. The switch provider 104 may include a processor 126, a memory 128, input/output ("I/O") interface(s) 130, and a network interface 132. The memory 128 may store data files 134 and various program modules, such as an operating system ("OS") 136, a database management system ("DBMS") 138, and the host module 140. The host module 140 may receive, process, and respond to requests from the client module 122 of the pharmacy computer 102, and may further receive, process, and respond to requests from the host module 172 of the payor computer 106.

The payor computer 106 may be associated with a pharmacy benefits manager (PBM), an insurance company, or another third-party payor. The payor computer 106 may include any processor-driven device that is configured for receiving, processing, and fulfilling requests from the pharmacy computer 102 or switch provider 104 related to adjudication or benefits determination of pharmacy claims requests, according to an example embodiment of the invention. The payor computer 106 may include a processor 158, a memory 160, input/output ("I/O") interface(s) 162, and a network interface 164. The memory 160 may store data files 166 and various program modules, such as an operating system ("OS") 168, a database management system ("DBMS") 170, and a host module 172. The host module 172 may receive, process, and respond to requests from the client module 122 of pharmacy computer 102, and may further receive, process, and respond to requests from the host module 140 of the switch provider 104. Those of ordinary skill in the art will appreciate that the payor computer 106 may include alternate and/or additional components, hardware or software as well.

The condition identification system 108 may be operative to identify, based on pharmacy claims, eligible patients that are candidates for having chronic medication conditions, according to an example embodiment of the invention. The condition identification system 108 may also be operative to provide information relating to the identified patients to one or more pharmacy computers 102, so that additional services, including MTM services, may be offered and/or administered to the eligible patients, according to an example embodiment of the invention. The condition identification system 108 may include a processor 127, a memory 129, input/output ("I/O") interface(s) 131, and a network interface 133. The memory 129 may store data files 135 and various program modules, such as an operating system ("OS") 137, a database management system ("DBMS") 139, and the host module 141. The host module 141 may receive, process, and respond to requests from the client module 122 of the pharmacy computer 102, and may further receive, process, and respond to requests from the host module 172 of the payor computer 106.

The network 110 may include any telecommunication and/or data network, whether public, private, or a combination thereof, including a local area network, a wide area network, an intranet, an internet, the Internet, intermediate hand-held data transfer devices, and/or any combination thereof and may be wired and/or wireless. The network 110 may also allow for real-time, off-line, and/or batch transactions to be transmitted between two or more of the pharmacy computer 102, the switch provider 104, the payor computer 106, and/or the condition identification system 108. While network 110 has been illustrated as a single network, it is to be understood that any other network configuration is possible. For example, network 110 may include a plurality of networks, each with devices such as gateways and routers for providing connectivity between or among networks 110. Instead of or in addition to a network 110, dedicated communication links may be used to connect the various devices in accordance with example embodiment invention. For example, the switch provider 104 may form the basis of network 110 that interconnects the pharmacy computer 102 and the payor computer 106.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration. By way of example, while the condition identification system 108 has been illustrated as distinct from the switch provider 104 or the payor computer 106, it will be appreciated that the functionality of condition identification system 108 described herein may likewise be incorporated, perhaps as software of computer-executable instructions, into the switch provider 104 or the payor computer 106.

Figure 2:
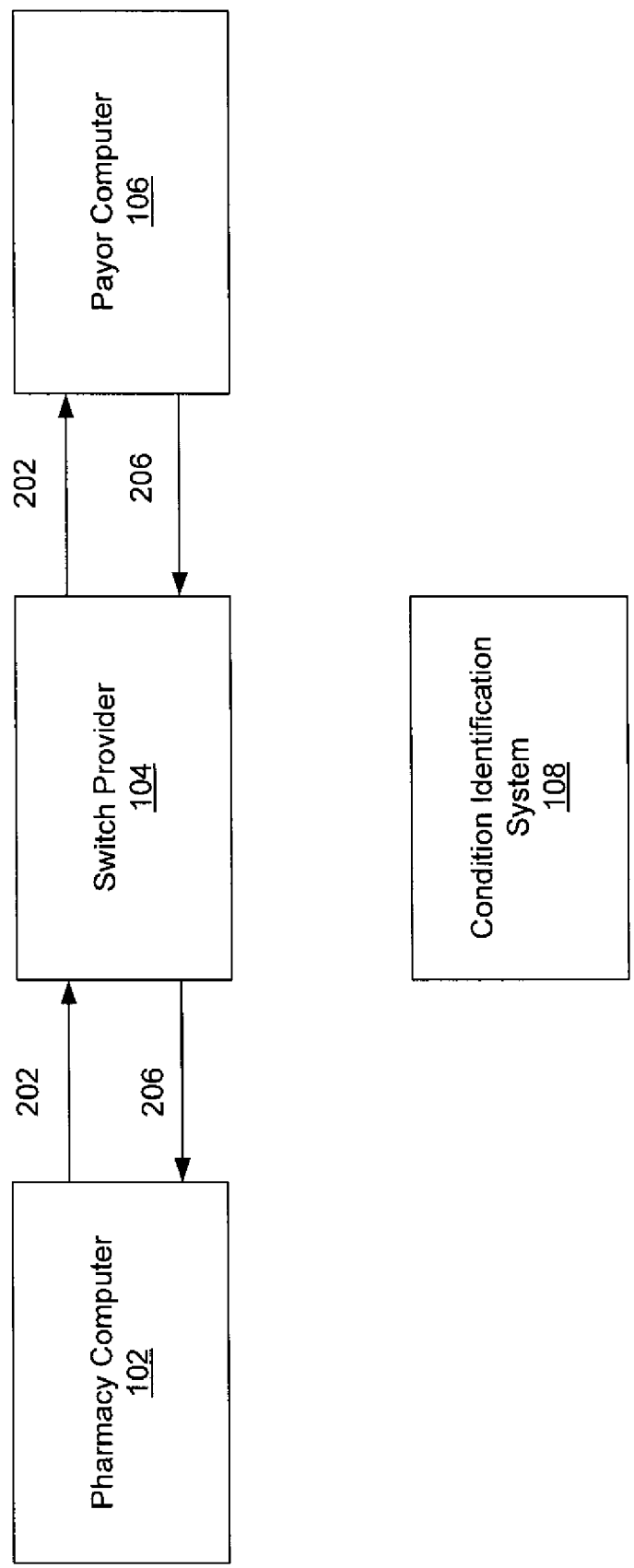
FIG. 2 illustrates an example block diagram for processing of pharmacy claim transactions, according to an example embodiment of the invention.
Figure 3:
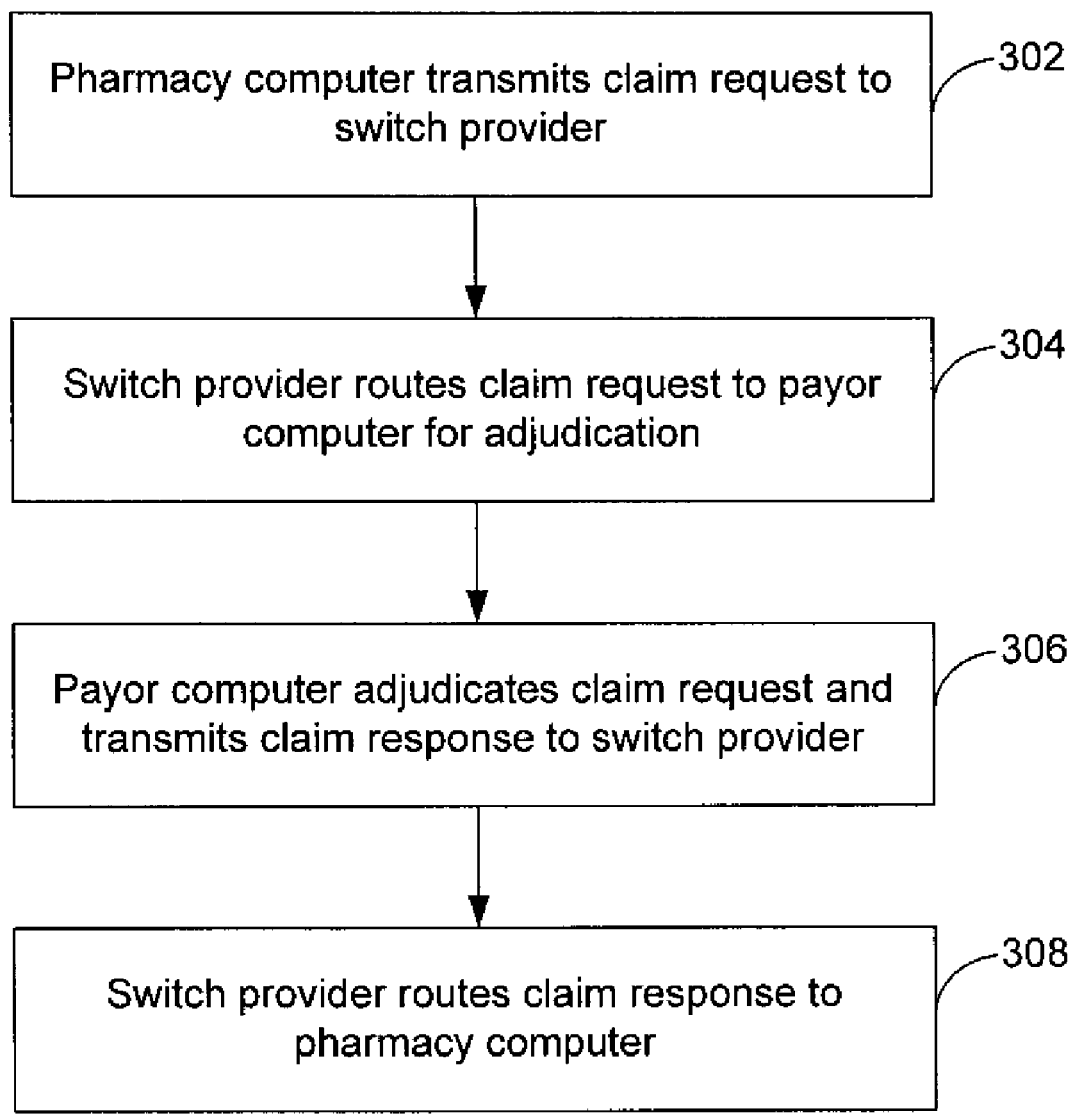
FIG. 3 illustrates a flow diagram from processing of pharmacy claim transactions, according to an example embodiment of the invention.

FIG. 2 illustrates an example block diagram for processing of pharmacy claim transactions, according to an example embodiment of the invention. The block diagram of FIG. 2 will be discussed in conjunction with the flow diagram of FIG. 3. Referring now to FIGS. 2 and 3, in block 302, the pharmacy computer 102 transmits a pharmacy claim request 202 on behalf of a patient to the switch provider 104. In an example embodiment of the invention, the pharmacy claim request 202 may include one or more of the following information:

an identification of the drug (e.g., National Drug Code (NDC)),
a quantity of the drug,
a price of the drug,
the pharmacy's usual and customary (U&C) price charged for the drug (e.g., a cash customer cost),
a date of the claim request,
a pharmacy identification number, and
patient information (e.g., identifier, name, address, and/or contact information).

It will be appreciated that while some example information has been illustrated for the example pharmacy claim request 202, it will be appreciated that alternate or additional information may also be included without departing from example embodiments of the invention. For example, the pharmacy claim request 202 may also include a Banking Identification Number (BIN)/Processor Control Number (PCN) for identifying a payor computer 106 as a destination of the pharmacy claim request 202.

In block 304, the switch provider 104 may receive the pharmacy claim request 202, and route or otherwise deliver the pharmacy claim request 202 to the payor computer 106 for further processing and/or adjudication. According to an example embodiment of the invention, the switch provider 104 may utilize the BIN/PCN in the received pharmacy claim request 202 to determine which payor computer 106 to route the pharmacy claim request 202 to. The switch provider 104 may also include a routing table, perhaps stored in memory 128, for determining which payor computer 106 to route the claim request 202 to. According to an example embodiment of the invention, the payor computer 106 may be associated with any pharmacy claims processing system, including those associated with a pharmacy benefits manager (PBM), an insurance company, or another third-party payor.

In block 306, the payor computer 106 receives and adjudicates the pharmacy claim request 202. In particular, the payor computer 106 may determine benefits coverage for the received pharmacy claim request 202 according to an adjudication process associated with eligibility, pricing, and/or utilization review. According to an example embodiment of the invention, the adjudication process may include determining a covered amount such as an insured amount, as well as a patient-responsible amount such as a co-pay or coinsurance amount. In block 306, the payor computer 106 transmits a claim response 206 to the switch provider 104. If the drug is covered, at least in part, by the payor computer 106, then the claim response 206 may include the covered amount, and the patient-responsible amount. On the other hand, if the drug is not covered by the payor 108, then the claim response 206 may be a rejected claim notice indicating that the drug is not covered by the payor computer 106. The claim response 206 may also include some or all of the information included in the pharmacy claim request 202, as discussed herein.

In block 308, the switch provider 104 may receive the claim response 206 from the payor computer 106. The switch provider 104 may then route or otherwise the deliver the claim response 206 to the pharmacy computer 102. The patient will then be responsible for paying any patient-responsible amount (e.g., co-pay or coinsurance amount) indicated by the claim response 206.

Figure 4:
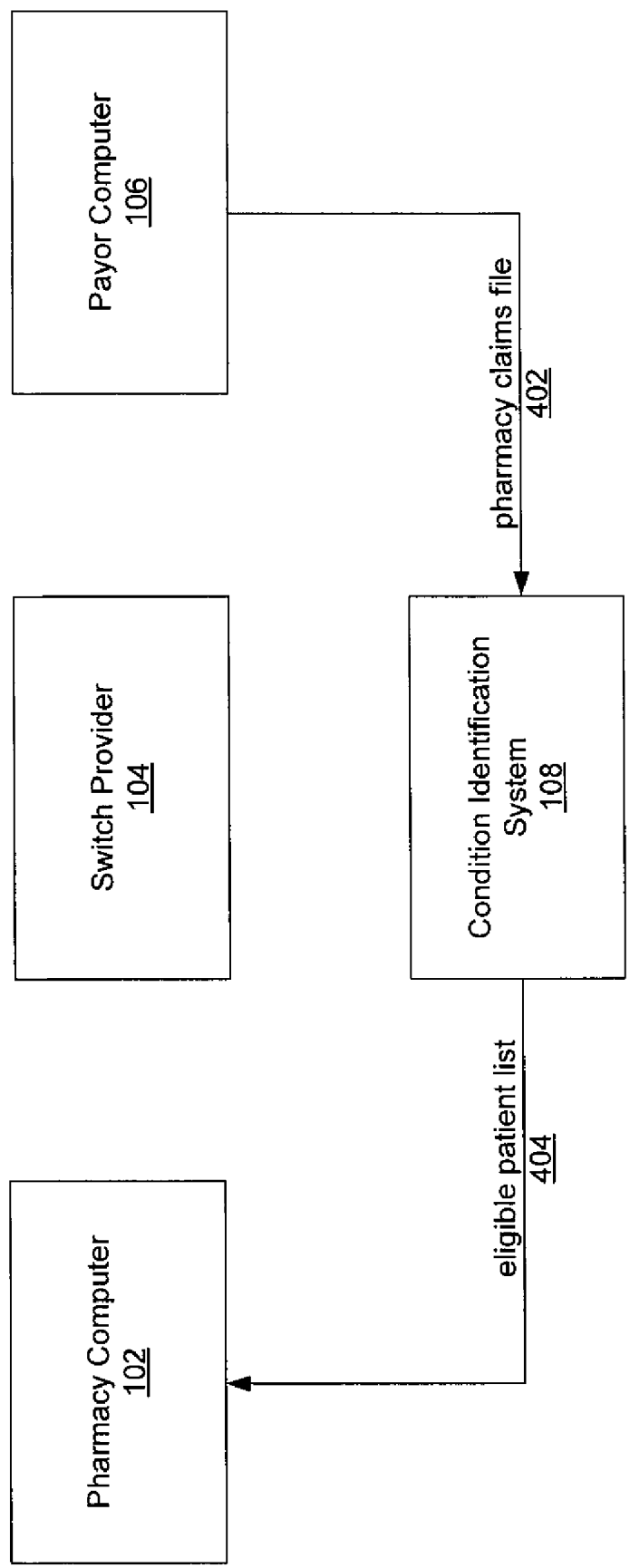
FIG. 4 illustrates an example block diagram for identifying, based upon pharmacy claims, eligible patients that are candidates for having chronic medical health conditions, according to an example embodiment of the invention.
Figure 5:
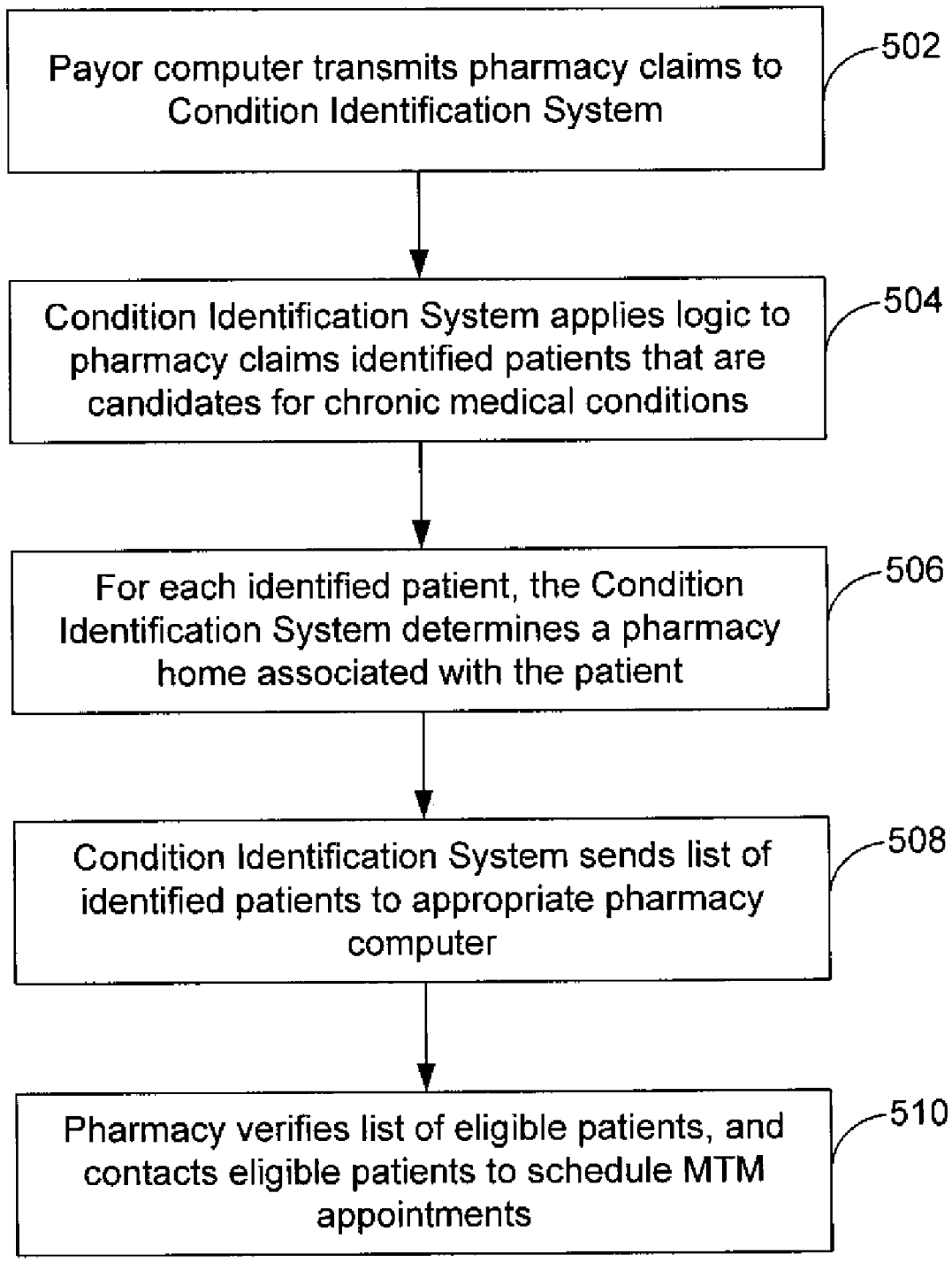
FIG. 5 illustrates an example flow diagram for identifying, based upon pharmacy claims, eligible patients that are candidates for having chronic medical health conditions, according to an example embodiment of the invention.

FIG. 4 illustrates an example block diagram for identifying, based upon pharmacy claims, eligible patients that are candidates for having chronic medical conditions, according to an example embodiment of the invention. The block diagram of FIG. 4 will be discussed in conjunction with the flow diagram of FIG. 5.

In block 502, the payor computer 106, or a data vendor computer associated with the payor, may transmit or otherwise deliver pharmacy claims, perhaps in one or more pharmacy claims files 402 that include the pharmacy claims, to the condition identification system 108. The pharmacy claims in the file 402 may be associated with medications previously filled by patients. According to an example embodiment of the invention, the pharmacy claims file 402 may include information associated with a plurality of pharmacy claim transactions, including:

a date associated with the pharmacy claim transaction,
an identification of the drug (e.g., National Drug Code (NDC)),
a pharmacy identification number, and
patient information (e.g., identifier, name, address, contact information, etc.).

It will be appreciated that a pharmacy claims file 402 may be provided by the payor computer 102 to the condition identification system 108 on a periodic basis (e.g., daily, weekly, monthly, quarterly, semi-annually, etc.), according to an example embodiment of the invention. Likewise, the pharmacy claims transactions included within the pharmacy claims file 402 may have occurred within a particular date range (e.g., within 1 month, 3 months, 6 months, etc.) of a current date or designated date, according to an example embodiment of the invention.

In block 504, the condition identification system 108 may receive the pharmacy claims, perhaps in a pharmacy claims file 402, from the payor computer 106. The condition identification system 108 may then apply logic or rules to the pharmacy claims to determine a list 404 of patients that may be candidates for having one or more chronic medical conditions, and that may be eligible to receive additional services, including MTM program services, according to an example embodiment of the invention. According to an example embodiment of the invention, the example logic or rules may generally involve the condition identification system 108 filtering or otherwise sorting the received pharmacy claims that are within a date range of interest (e.g., within the last 3 months, 6 months, etc) to obtain the active prescriptions for further analysis. It will be appreciated, however, that in other example embodiments of the invention, the condition identification processor 108 may consider all of the received pharmacy claims as active prescriptions as well.

Still referring to block 504, the condition identification processor may analyze the active prescriptions, and in particular, the medications or drugs associated with the active prescriptions. Indeed, the prescribed medications or drugs may be indicative or suggestive of, or otherwise correlated with, whether a patient may be a candidate for having a chronic medical condition. For example, some prescribed medications or drugs are used solely to treat chronic medical conditions, and thus any of these prescribed medications or drugs are directly indicative of or correlated with a chronic medical condition. By way of example, if a patient has any active prescriptions for a medication or drug that is on a Diabetes condition list maintained or accessible by the condition identification system 108, then the condition identification system 108 may determine that the patient is a candidate for a chronic medical condition. Indeed, prescribed medications or drugs on the Diabetes condition list may have a very high probability of being used treating diabetes. However, other prescribed medications of the active prescriptions may have multiple uses, for example, for both acute and chronic medical conditions. In this scenario, the condition identification system 108 may determine that a patient is a candidate for having a chronic medical condition based upon the following rules or logic:

the patient having at least two active prescriptions from any 2 chronic disease condition lists (e.g., at least 2 prescribed medications that can be used to treat 2 different chronic medical conditions), and at least a total of 4 or more active prescriptions;

the patient having least one active prescription from any 1 chronic disease condition list, and a total of 5 or more active prescriptions; and/or the patient having at least 6 or more active prescriptions.

It will be appreciated that many variations of the example rules or logic for determining that a patient is a candidate for having a chronic medical condition are possible. Indeed, the threshold numbers for the numbers of chronic disease condition lists and/or total active prescriptions that are to be satisfied before determining a patient is an eligible candidate for a chronic medical condition may be varied without departing from example embodiments of the invention.

According to an example embodiment of the invention, the chronic disease condition lists described herein may comprise different classifications, each having one or more associated medications. For example, the condition identification system 108 may maintain or otherwise have access to chronic disease conditions lists for one or more of the following categories, which include, but are not limited to: diabetes; respiratory; asthma; congestive obstructive pulmonary disorder (COPD); hypertension; coronary artery disease (CAD); congestive heart failure; dyslipidemia; depression, or a combination thereof. Likewise, for each chronic disease condition list, there may be one or more drugs or medications identified as being used to treat the associated conditions. Accordingly, by determining whether one or more active prescriptions are associated with one or more chronic disease condition lists and active prescriptions, the condition identification system 108 may determine that the patient is a candidate for a chronic medical condition.

In block 506, for each identified eligible patient, the condition identification system 108 may also determine a pharmacy home for the identified eligible patient. The pharmacy home may determine which pharmacy location offers additional services to the identified eligible patients. According to an example embodiment of the invention, the pharmacy home for the identified eligible patient may be based upon the number of prescriptions previously filled by the patient at a particular pharmacy in a particular time frame, or the total amount of money previously spent by the patient at a particular pharmacy. The pharmacy home for a particular patient may be set to the particular pharmacy where the patient filled the largest number or majority of prescriptions within a particular time frame (e.g., last 3 months, 6 months, etc.). Where there is a tie between two or more pharmacies for a pharmacy home, the highest total amount of money spent at a particular pharmacy within a particular time frame may serve as a tie breaker.

In block 508, the condition identification system 108 may deliver a list 404 of identified eligible patients to the appropriate pharmacy computer 102 corresponding to the identified home pharmacy for those patients. The eligible patients list 404 may be in a comma separated variable (CSV) or Excel format, although other formats may be utilized as well. The eligible patients list 404 may include some or all of the following information for each eligible patient:

patient information (e.g., name, address, contact information) or other unique identifier of the patient;

prescription information (e.g., claims amount, name of prescriptions, etc.) for the patient;

identification of the pharmacy home of the patient; and/or one or more identified medical conditions (e.g., a chronic medical conditions such as diabetes, heart condition, etc.) of the patient.

In block 510, the pharmacy and/or the pharmacy computer 102 associated with the pharmacy home may verify the eligible patients list 404, and may further contact eligible patients from the list 404 to offer additional services, including MTM services and/or other consultations regarding the patient's medications and/or treatments associated with the chronic medical condition. According to an example embodiment of the invention, a pharmacy employee or another healthcare provider may contact the patient by telephone, email, facsimile, postal mail, and the like to schedule an MTM appointment. On the other hand, the pharmacy computer 102 may direct a paper mailing, or an electronic communications to the patient via telephone recording, facsimile, email, or another other electronic message, to the patient to schedule an MTM appointment. The MTM appointment may be scheduled to occur at a location of the pharmacy or other healthcare provider, according to an example embodiment of the invention.

It will be appreciated that many variations of the above-described embodiments are possible. As an example, the condition identification system 108 may deliver the eligible patient list 404 to payor computer 106 instead of the pharmacy computer 102. In this embodiment, the payor associated with the payor computer 106 may initiate communications with the identified patient to offer consultations or other services in accordance with an MTM program. Alternatively, the payor computer 106 may provide the eligible patient list 404 to the pharmacy computer 102.

According to an example embodiment of the invention, the pharmacist or other healthcare provider may perform a variety of consultations and services with the patient, including comprehensive medication review and assessment (CMR/A) Services. Examples of these CMR/A Services provided by a pharmacist or healthcare provider may include:

Performing of an initial CMR/A to identify, resolve and prevent medication-related problems, including adverse drug events; this includes performing medication reconciliation for a patient discharged from the hospital or long term care setting;

Obtaining necessary assessments of the patient's health status;

Formulating a medication treatment plan;

Providing an updated Personal Medication Record (PMR) and Medication Action Plan (MAP) to each patient following each CMR/A visit;

Providing information, support services, and resources designed to enhance patient adherence with the patient's therapeutic regimens;

Providing verbal education and training designed to enhance patient understanding and appropriate use of the patient's medications;

Performing follow up medication reviews to monitor and evaluate the patient's response to therapy, including safety and effectiveness of target medications;

Documenting the care delivered and communication of essential information to the patient's primary care providers;

Referring the patient to an appropriate health care provider if necessary;

Coordinating and integrating medication management services within the broader health care system; and/or Notifying appropriate prescriber(s) of each CMR/A service provided and sending a copy of the PMR and MAP. If authorizations to change specific medications are needed, the specific prescriber will be notified.

In addition to providing CMR/A services, the pharmacist or other healthcare provider may also provide condition-specific medication management services, including those for hypertension, asthma, hyperlipidemia, anticoagulation, tobacco cessation, chronic kidney disease, congestive heart failure, osteoporosis, chronic obstructive pulmonary disease, depression, HIV, and transplants. The condition-specific, standardized assessments developed using clinical guidelines may be provided to pharmacists via a MTM software system operable with the healthcare provider computer 102 to aid in the provision of services to patients with specific conditions. Each assessment will be designed to complement healthcare provider and payor-sponsored disease management programs. The program standards may be consistent with industry best practices, according to an example embodiment of the invention.

For each patient that the pharmacist or healthcare provider consults with or provides services to, the pharmacist or healthcare provider may document the patient assessment. The documented information may include some or all of the following:

Patient name
Current medical conditions
Patient address and telephone number
Significant past medical history
Patient gender
Allergies
Patient's date of birth
Primary physician and contact information
Date of encounter
Date of documentation
Time spent with patient
Reason for CMR/A (which risk factors, referral by plan, etc.)
List of all prescription (including medications from specialty pharmacies, mail order, samples and medications purchased on the internet) and nonprescription drugs/herbals with their indications, doses, and directions
List of all relevant medical devices
List of all dietary supplements and herbal products
Assessment of drug problems identified, including but not limited to:
    Appropriate indications for each medication
    Adherence to medication regimens
    The need for additional medications (based on clinical guidelines or patient-specific issues)
    Appropriate dosing to meet goals of therapy and avoid toxicity
    Adverse events potentially caused by medications
    Effectiveness and safety of current drug therapy
    Written plan including goals and actions needed to resolve issues of current drug therapy
    Evaluation of success in meeting goals of medication treatment plan
    Information, instructions and resources delivered to the patient
    Content of pharmacist's communications to patient's other health care providers Suggested Information:
    Alcohol and tobacco use history
    Immunization history
    Other pertinent patient information.

It will be appreciated that other information may be documented by the pharmacist or healthcare provider as desired or necessary. Additionally, pharmacist or healthcare provider that provides consultation or MTM services to an eligible patient may be provided with compensation from a payor or another entity.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:
1. A computer-implemented method, comprising:
receiving, by a condition identification system comprising one or more computers, at least one pharmacy claim associated with a patient, wherein each pharmacy claim is associated with a medication previously filled by the patient;

identifying, by the condition identification system, the patient as a candidate for at least one chronic medical condition by analyzing the at least one pharmacy claim associated with the patient;

determining, by the condition identification system, a pharmacy home for the patient based upon a history of prior pharmacy claims associated with the patient, wherein the pharmacy home is determined by selecting the pharmacy location that is designated by a majority of the prior pharmacy claims associated with the patient; and transmitting, by the condition identification system to a pharmacy computer associated with the pharmacy home, an identification of the patient that is the candidate for at least one chronic medical condition, wherein the patient is offered at least one service by the pharmacy home based upon the transmitted identification of the patient.

2. The computer-implemented method of claim 1, wherein the condition identification system receives a plurality of pharmacy claims for a plurality of patients, including the at least one pharmacy claim associated with the patient.

3. The computer-implemented method of claim 2, wherein the plurality of claims is received in a pharmacy claims file associated with a payor computer, wherein the plurality of claims have been previously adjudicated by the payor computer.

4. The computer-implemented method of claim 1, wherein, the at least one pharmacy claim associated with the patient comprises a plurality of pharmacy claims associated with the patient, wherein at least one of the plurality of pharmacy claims is associated with a first medication.

5. The computer-implemented method of claim 4, wherein the condition identification system identifies the patient as the candidate for at least one chronic medical condition at least in part by determining that the first medication is associated with a treatment for a first chronic medical condition.

6. The computer-implemented method of claim 5, wherein the condition identification system identifies the patient as the candidate for at least one chronic medical condition by further determining that a total number of the plurality of pharmacy claims associated with the patient within a time frame exceeds a threshold number.

7. The computer-implemented method of claim 5, wherein at least one of the plurality of pharmacy claims is associated with a second medication different from the first medication, wherein the condition identification system identifies the patient as the candidate for at least one chronic medical condition by further determining that the second medication is associated with a treatment for a second chronic medical condition different from the first chronic medical condition.

8. The computer-implemented method of claim 1, wherein the pharmacy home offers the patient medication therapy management (MTM) services based upon the transmitted identification of the patient to the pharmacy computer.

9. The computer-implemented method of claim 1, wherein if no pharmacy location is designated by a majority of the prior pharmacy claims associated with the patient, then the condition identification system determines the pharmacy home for the patient by selecting, based upon the prior pharmacy claims, the pharmacy location where the patient has spent the most amount of money.

10. A system, comprising:
a memory for storing computer-executable instructions;
a processor configured to access the memory and to execute the computer-executable instructions to:

receive, from a payor computer, at least one pharmacy claim associated with a patient, wherein each pharmacy claim is associated with a medication previously filled by the patient, identify, based upon an analysis of the at least one pharmacy claim, the patient as a candidate for at least one chronic medical condition, determine a pharmacy home for the patient based upon a history of prior pharmacy claims associated with the patient, wherein the pharmacy home is determined by selecting the pharmacy location that is designated by a majority of the prior pharmacy claims associated with the patient, and transmit, to a pharmacy computer associated with the pharmacy home, an identification of the patient that is the candidate for at least one chronic medical condition, wherein the patient is offered at least one service by the pharmacy home based upon the transmitted identification of the patient.

11. The system of claim 10, wherein the processor is configured to receive a plurality of pharmacy claims for a plurality of patients, including the at least one pharmacy claim associated with the patient.

12. The system of claim 11, wherein the plurality of claims is received in a pharmacy claims file, wherein the plurality of claims have been previously adjudicated by the payor computer.

13. The system of claim 10, wherein the at least one pharmacy claim associated with the patient comprises a plurality of pharmacy claims associated with the patient, and wherein at least one of the plurality of pharmacy claims is associated with a first medication.

14. The system of claim 13, wherein the processor is configured to identify the patient as the candidate for at least one chronic medical condition at least in part by determining that the first medication is associated with a treatment for a first chronic medical condition.

15. The system of claim 14, wherein the processor is configured to identify the patient as the candidate for at least one chronic medical condition by further determining that a total number of the plurality of pharmacy claims associated with the patient within a time frame exceeds a threshold number.

16. The system of claim 14, wherein at least one of the plurality of pharmacy claims is associated with a second medication different from the first medication, wherein the processor is configured to identify the patient as the candidate for at least one chronic medical condition by further determining that the second medication is associated with a treatment for a second chronic medical condition different from the first chronic medical condition.

17. The system of claim 10, wherein the pharmacy home offers the patient medication therapy management (MTM) services based upon the transmitted identification of the patient to the pharmacy computer.

18. The system of claim 10, wherein if no pharmacy location is designated by a majority of the prior pharmacy claims associated with the patient, then the processor is configured to determine the pharmacy home for the patient by selecting, based upon the prior pharmacy claims, the pharmacy location where the patient has spent the most amount of money.

* * * * *